United States Patent
Banse et al.

(10) Patent No.: US 6,649,582 B1
(45) Date of Patent: Nov. 18, 2003

(54) BLEACH CATALYSTS AND FORMULATIONS CONTAINING THEM

(75) Inventors: Frédéric Banse, Orsay (FR); Riccardo F. Carina, Geneva (CH); Michel G. J. Delroisse, Wirril (GB); Jean-Jacques Girerd, Orsay (FR); Ronald Hage, Vlaardingen (NL); Jalila A. Simaan, Orsay (FR); David Tetard, Wirril (GB)

(73) Assignee: Unilever Patent Holdings B.V., Vlaardingen (NL)

( * ) Notice: Subject to any disclaimer, the term of this patent is extended or adjusted under 35 U.S.C. 154(b) by 0 days.

(21) Appl. No.: 09/719,679

(22) PCT Filed: Jun. 10, 1999

(86) PCT No.: PCT/GB99/01850
§ 371 (c)(1),
(2), (4) Date: Jul. 12, 2001

(87) PCT Pub. No.: WO99/65905
PCT Pub. Date: Dec. 23, 1999

(30) Foreign Application Priority Data

| Jun. 15, 1998 | (GB) | ............................................... | 9812916 |
| Sep. 1, 1998 | (GB) | ............................................... | 9819046 |
| Mar. 19, 1999 | (GB) | ............................................... | 9906474 |

(51) Int. Cl.$^7$ ............................... C11D 7/32; C11D 7/54
(52) U.S. Cl. .................. 510/376; 510/311; 252/186.33; 502/207; 502/325; 502/338; 8/111
(58) Field of Search ................................. 510/376, 311; 252/186.33; 502/207, 325, 338; 8/111

(56) References Cited

FOREIGN PATENT DOCUMENTS

| WO | WO 94/26276 | 11/1994 |
| WO | WO 96/06154 | 2/1996 |
| WO | WO 98/10286 | 3/1998 |
| WO | WO 98/39406 | * 9/1998 |

* cited by examiner

Primary Examiner—Gregory Delcotto
(74) Attorney, Agent, or Firm—Morgan Lewis & Bockius LLP

(57) ABSTRACT

The present invention relates to new macrocyclic bleach catalysts, to formulations comprising these catalysts, as well as bleaching processes which employ these catalysts. These catalysts exhibit unexpected hydrolytic stability, as well as stability against metal abstraction by metal abstracting agents.

9 Claims, No Drawings

BLEACH CATALYSTS AND FORMULATIONS CONTAINING THEM

TECHNICAL FIELD

The present invention relates to new macrocyclic bleach catalysts, to formulations comprising these catalysts, as well as bleaching processes which employ these catalysts.

BACKGROUND OF THE INVENTION

Metal ion catalysis of oxygen bleaches, particularly in fabric washing processes, is well known. In these systems, a metal such as manganese, generally attached to a suitable ligand is exposed to the fabric together with an oxygen bleach such as hydrogen peroxide. A known disadvantage of such systems is that the metal species can be abstracted from the ligand and oxidised to form an insoluble oxide precipitate which deposits at the fabric surface.

Two mechanisms have been proposed for catalysed bleaching, in one the oxygen bleach is decomposed in the presence of the catalyst to a short-lived but highly active species such as the hydroxyl radical. In the other proposed mechanism, the oxygen bleach reacts with the catalyst to form an intermediate species which either transfers oxygen or abstracts hydrogen atoms or electrons to the substrate. As will be appreciated, the first type of reaction is relatively non-specific as regards the substrate while the second is likely to be influenced strongly by the nature of the substrate and its reactivity with the intermediate.

While the non-specific reaction is likely to attack most materials which are susceptible to bleaching, it is not suitable for many applications. There is a need for electron or oxygen transfer systems which are capable of reacting with structures such as catechols, and curcumin etc., which are found in the components of, for example, wine and tea stains (catechol) or curry stains (curcumin). It is important that the components of such electron or oxygen transfer systems are hydrolytically stable so as avoid the disadvantages mentioned above.

Bottino et al (*J. Org. Chem.* 1988, 53, 3521–3529) disclose the synthesis of symetrical N-tosyl aza macrocycles. Kruger (*Chem. Ber.* 1995, 128, 531–539) discloses the N,N-Dimethyl-2,11-diazo[3.3](2,6)pyridinophane (NNDDP) complexes of copper, nickel and cobalt. The corresponding vanadium complex is disclosed in Inorg. Chem. (1996), 35, 3533. NNDDP is a macrocyclic ligand. Other manganese macrocyclic ligand complexes are known as mimics of superoxide dismutase form Riley et. al. (*J. Am. Chem. Soc.*, 1994, 116, 387–388). However, these are not aryl ligands.

Koch et. al. (*Angew. Chem. Its. Ed Engl.*, 1995, 34, No 23/24 p 2671–2674) (hereinafter called the "First Koch Reference") disclose that certain Iron III complexes of NNDDP are capable of mimicking the biological activity of intradiol-cleaving catechol dioxygenases and converting catechols, in the presence of oxygen to the corresponding muconic acid. The synthesis of certain eight-co-ordinate iron II and iron III complexes of bis(2,11-diaza[3.3](2,6) pyridinophane, i.e. certain non-methylated analogues of NNDDP is described by Koch et. al. in *Angew. Chem., Int. Ed Engl.*, (1996), 35(4), 422–4 (hereinafter called the "Second Koch Reference"). However, there is no disclosure of the suitability of such materials as bleach catalysts for detergent products, nor any description of corresponding iron complexes having a lower co-ordination number.

BRIEF DESCRIPTION OF THE INVENTION

It has now been discovered that certain novel ligands which are NNDDP analogues have novel activities in themselves and furthermore in complex with various metals, also have better activity than known iron III NNDDP complexes. They exhibit unexpected hydrolytic stability, as well as stability against metal abstraction by metal abstracting agents. Furthermore, these new materials show unexpected activity with air, or molecular oxygen or other oxygenated bleaching materials such as peroxides, persalts or peracids, against catechol and catechol-like materials which form a significant component of several common laundry stains. They could also find application in a wide range of other uses where a bleaching effect is desired.

In general, the invention is based upon a macrocyclic ligand of formula (I):

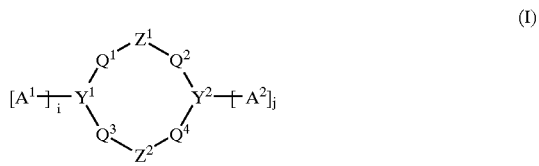

(I)

wherein $Z^1$ and $Z^2$ are independently selected from monocyclic or polycyclic aromatic ring structures optionally containing one or more heteroatoms, each aromatic ring structure being optionally substituted by one or more substituents $Y^1$ and $Y^2$ are independently selected from C, N, O, Si, P and S atoms $A^1$ and $A^2$ are independently selected from hydrogen, alkyl, alkenyl and cycloalkyl (each of alkyl, alkenyl and cycloalkyl being optionally substituted by one or more groups selected from hydroxy, aryl, heteroaryl, suphonate, phosphate, groups of formulae $(G^1)(G^2)N$—$G^3OC(O)$—, $G^3O$— and $G^3C(O)$—, wherein each of $G^1$, $G^2$ and $G^3$ is independently selected from hydrogen and alkyl, and electron donating and/or withdrawing groups in addition to any amongst the foregoing), electron donating groups and electron withdrawing groups;

i and j are selected from 0, 1 and 2 to complete the valency of the groups $Y^1$ and $Y^2$ each of $Q^1$–$Q^4$ is independently selected from groups of formula

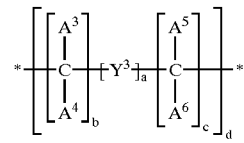

wherein 10>a+b+c+d>=2;

each $Y^3$ is independently selected from O, S, SO, $SO_2$, $(G^1)(G^2)N$— (wherein $G^1$ and $G^2$ are as hereinbefore defined), C(O), monocyclic or polycyclic aryl, monocyclic or polycyclic heteroaryl, P and P(O);

each of $A^3$–$A^6$ is independently selected from the groups hereinbefore defined for $A^1$ and $A^2$; and wherein any two or more of $A^1$–$A^6$ together may optionally form a bridging group, provided that if $A^1$ and A2 are linked without simultaneous linking also to any of A3–A6, then the bridging group linking $A^1$ and $A^2$ must contain at least one carbonyl group.

For the avoidance of doubt, throughout this specification, "=<" means "less than or equal to" and ">=" means "greater than or equal to".

Thus, a first aspect of the present invention provides a novel ligand of formula (I) as hereinbefore defined.

In formula (I), $Z^1$ and $Z^2$ are preferably the same. Preferably $Z^1$ and/or $Z^2$ are selected from nitrogen-containing monocyclic aryl groups, for example linkages constituted by pyridine, pyrrole, imidazole and pyrazine rings. Of these, pyridine is the most preferred. Any of the foregoing is optionally substituted, e.g. by one or more electron withdrawing and/or electron donating groups.

$Y^1$ and Y2 are preferably both the same. In any event, preferably $Y^1$ and/or Y2 is selected from nitrogen and carbon atoms.

In the definitions of $A^1$ and $A^2$, alkyl groups preferably have from 1 to 6 carbon atoms, alkenyl groups preferably have from 2–6 carbon atoms, cycloalkyl groups preferably have from 5 to 9 carbon atoms and aryl and heteroaryl groups are preferably monocyclic and have from 5 to 9 carbon atoms or carbon+heteroatoms respectively. Wherever else alkyl, akenyl, cycloalkyl, aryl and heteroaryl moieties are mentioned in this specification, they preferably have the same number of (carbon) atoms as in this definition of $A^1$ and $A^2$, unless explicitly recited to the contrary.

In the definition of $Q^1$–$Q^4$, d is preferably 1 or 2, most preferably 1. It is also preferred that a+b+c=1, 2 or 3. $Y^3$(when present) is preferably —NH$_2$— or —NHCO—. It is especially preferred that any of $Q^1$–$Q^4$ is —CH$_2$—. Preferably, $Q^1$–$Q^4$ are all the same.

Throughout this specification, any reference to electron donating or withdrawing groups refers to any such group or groups known to those skilled in the art. However, typical electron withdrawing groups are halo (e.g. chloro or fluoro), $C_{1-6}$alkoxy (e.g. methoxy), hydroxy, hydroxyalkyl, (optionally mono-or di-substituted) amine groups, (optionally mono- or di-substitued) thiol groups, carboxyl, ester, amide, substituted carbonyl groups in general, nitrile, nitro (optionally substituted) sulphonyl, alkenyl e.g. vinyl, ethynyl, phenyl, quarternary ammonium (+) and sulphonium (+) groups. Aryl groups in general may also be used.

Typical electron donating groups include $C_{1-6}$alkyl (especially methyl), $C_{5-9}$cycloalkyl, carboxy anion and hydroxy anion groups.

As will be explained in more detail hereinafter, the ligands of formula(I) may be used in the form of complexes with an appropriate metal, or, in some cases, in non-complexed form, in which case they rely upon complexing with a metal supplied in the form of a separate ingredient in the detergent composition, provided for supplying that metal or even, complexing with a metal found as a trace element in tap water. However, where the ligand alone or in complex from carries a (positive) charge, a counter anion is necessary. The ligand or complex may be formed as a neutral species but it is often advantageous for reasons of stability or ease of synthesis, to have a charged species with appropriate anion.

A second aspect of the present invention provides a ligand of formula (I) which is ion-paired with a counter-ion, which ion-pairing is novel, the complex being denoted by formula (II)

$$[H_xL]^zY_q \tag{II}$$

wherein
H is an hydrogen atom;
Y is a counter anion, the type of which is dependent on the charge of the complex;
x is an integer such as that one or more heteroatoms in L is protonated;
z represents the charge of the complex and is an integer which can be positive or zero;
q=z/[charge of Y]; and
L is a ligand of formula (I) as hereinbefore defined.

A third aspect of the present invention comprises a metal complex of formula (III) based on the ion pairing of formula (II) thus

$$[M_xL]^zY_q \tag{III}$$

wherein L, Y, x, z and q are as defined in formula (II) and M is a metal selected from manganese in oxidation states II, III, IV or V, iron II, III, IV or V, copper I, II or III, cobalt I, II or III, nickel I, II or III, chromium II, III or IV, tungsten IV, V or VI, palladium V, rhuthenium II, III or IV, vanadium III or IV and molybdenum IV, V or VI.

Especially preferred are the complexes of formula (III) wherein M represents manganese, cobalt, iron or copper.

A fourth aspect of the present invention comprises a bleaching composition comprising a ligand of formula (I) and/or an ion pair of formula (II) and/or a complex of formula (III). Particularly preferred are such compositions further comprising a surfactant. In the case of compositions according to the fourth aspect of the invention, no further bleach component need be included of catalytic free oxygen bleaching is the mode of bleaching. In other cases, a bleach or bleach system, especially a peroxygen bleach or bleach system will be included.

The invention further extents to use of compositions according to the fourth aspect of the invention for laundry cleaning, hard surface cleaning (including cleaning of lavatories, kitchen work surfaces, floors, mechanical ware washing etc.), as well as other uses where a bleach is needed, for example waste water treatment or pulp bleaching during manufacture of paper, dye transfer inhibition, starch bleaching, sterilisation and/or whitening in oral hygiene preparation, contact lens disinfection.

The following ligands of formula (I), ion pairs of formula (II) and complexes of formula (III) are known per se, but their incorporation bleach, or detergent or other household cleaning or laundry products, with or without the presence of an auxiliary bleach or bleach system is new, as is their use as bleaching catalysts with or without the simultaneous application of an auxiliary bleach or bleach system. To the extent that they are known per se, they are hereby disclaimed from the scope of the present invention but are included where their incorporation in any such product formulation or their use as bleaching catalysts is new. Hereinafter, these prior art materials are referred to as the "Known Ligands", the "Known Ion Pairs" and the "Known Complexes", respectively.

In the following, —Ph denotes a phenyl group and —Py— denotes a pyridyl group in the configuration

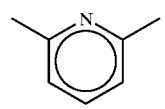

1. Kim W. et. al., *Inorg. Chem.*, (1995), 35, 2225 discloses a ligand of formula (I) where $Q^1$ to $Q^4$ are all —CH$_2$—, $Z^1$ and $Z^2$ are both —Py—, $Y^1$ and $Y^2$ are both nitrogen, i and j are both 1 and $A^1$ and $A^2$ both represent —CH$_2$—CO$_2$H.
2. The ligand of formula (I) wherein $Q_1$ to $Q^4$ are all —CH$_2$—, $Z^1$ and $Z^2$ are both —Py—, $Y^1$ and $Y^2$ are both nitrogen, i and j are both 1 and A and A2 are both hydrogen is known and in the following combinations:
   (i) complexes with lithium: Cesario M. et. al., *Helv. Chim. Acta*, (1991), 74, 1157

(ii) complexes with $Fe^{II}$, $Fe^{III}$ and $(ClO_4)_2$ counter-ion: Koch. W. O., *Angew. Chem. Int. Ed Engl.*, (1996), 35, 422(i.e. the Second Koch Reference)

(iii) complexes with $Co^{II}$ and $Ni^{II}$ $[CoL_2]X_2$ and $[NiL_2]$ $X_2$: Koch et. al., *Chem, Commun.*, (1997), 2237.

3. The ligand where $Q^1$ to $Q^4$ are all —$CH_2$—, $Z^1$ and $Z^2$ are both —Py—, $Y^1$ and Y2 are both nitrogen, i and j are both 1 and $A^1$ and $A^2$ are both hydrogen or both methyl are known from:
   (i) Takemura H. et. at., *Tetrahedroni Lett.*, (1988), 29, 1031
   (ii) Bottino F. et. al., *J. Org. Chem.*, (1988), 53, 3521
   (iii) Bottino F. et al., *Heterocycles*, (1985), 23, 1881.

4. The ligand where $Q^1$ to $Q^4$ are all —$CH^2$—, $Z^1$ and $Z^2$ are both —Py—, $Y^1$ and $Y^2$ are both nitrogen, i and j are both 1 and $A^1$ and $A^2$ are both hydrogen or both methyl are known in the following complexes:
   (i) complex with $Ru^{III}$ with $Cl_2$ counter-ion: Sakala H., *Bull. Chem. Soc. Jpn.*, (1990), 63, 1822
   (ii) complex with $Cu^{III}$ and $Cl_2$ counter-ion: Fronczek F. R. et.al., *Inorg. Chem.*, (1989), 28, 1419
   (iii) complex with $Fe^{III}$ and catechol(ate): Koch W. O. et. al., *Angew. Chem. Int. Ed. Engl.*, (1995), 34, 2671(i.e. the First Koch Reference)
   (iv) complexes with $Cu^{II}$, $Co^{II}$, $Ni^{III}$, all with $Cl_2$ counter-ion: Kruger et.al., *Chem. Ber.*, (1995), 128, 531
   (v) complex with Mo and $(CO)_3$: Herald K. et. al., *Eur. J Inorg. Chem.*, (1998), 1381
   (vi) complexes with $Fe^{II}$ or $Fe^{III}$ and semiquinone: Koch, W. O. et. al., *Chem. Eur. J.*, (1998), 4, 1255
   (vii) complex with $Fe^{III}$ and 1,2 dithiolbenzene: Koch W. O., *Chem. Eur. J.*, (1988), 4, 686.
   (viii) complex with V and $Cl_2$ counter-ion: Kelvin H. et. al., *Inorg. Chem.*, (1996), 35, 3533.

5. Two or three ligands of formula (I) linked in cyclic configuration wherein, in each, $Q^1$ to $Q^4$ are all —$CH_2$—, $Z^1$ and $Z^2$ are both —Py—, $Y^1$ and $Y^1$ are both nitrogen and $A^1$ and $A^2$ are bridging groups, where the $A^1/A^2$ bridging pairs are all —$CH_2$—Py—$CH_2$— bridges, are known, from Takemura H. et. al., *J Chem. Soc. Perkin Trans* 1, (1996), 3, 277.

6. Two ligands of formula (I) linked in cyclic configuration wherein in each, $Q^1$ to $Q^4$ are all —$CH_2$—, $Z^1$ and Z2 are both —Py—, $Y^1$ and $Y^2$ are both nitrogen and both $A^1/A^2$ bridging pairs are —$CH_2$—CH=CH—$CH_2$— are known and in complex with $Cu^{II}$ with $CN^-$ counter-ion from Warzeskz S. et.al., *Chem. Commun.*, (1996), 499.

7. The ligand of formula (I) wherein $Q^1$ and $Q^3$ are both —$CH_2$—, i=1, $A^1$=—$CH_2$—Ph and —$Z^2$—$Q^4$—$Y^2$ $(A_j^2)$—$Q_2$— is —(—Py—$CH_2$—N($CH_2$—Ph)—$CH_2$—)_2— is known from Lee G. et. al., *Chem. Lett.*, (1996), 873.

8. The ligand of formula (I) wherein $Q^1$ to $Q^4$ are all —$CH_2$—, $Z^1$ and $Z^2$ are both Py, $Y^1$ and $Y^2$are both nitrogen, i and j are both 1 and $A^1$ and $A^2$ are both t-butyl is known from Che C. M., *Polyhedron*, (1994), 13, 771.

A preferred sub-class of complexes of formula (III) comprises the iron bleach catalysts of formula (IV).

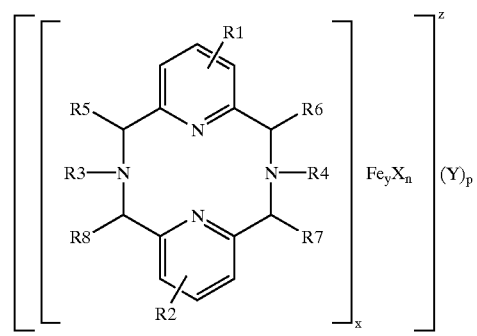

wherein Fe represents an iron atom in oxidation state II or III, X is a group which is either a bridge or is not a bridge between iron atoms, Y is a counter-ion, x and y being >=1, 0=<n=<3, and z being the charge of the metal complex, and p=z/ charge of Y; $R_1$ and $R_2$ being independently one or more ring substituents selected from hydrogen and electron donating and withdrawing groups, $R_1$–$R_8$, being independently hydrogen, alkyl, hydroxyalkyl, alkenyl or variants of any of these when substituted by one or more electron donating or withdrawing groups.

Another preferred sub-class of complexes of formula (III) comprises the manganese bleach catalysts of formula (V):

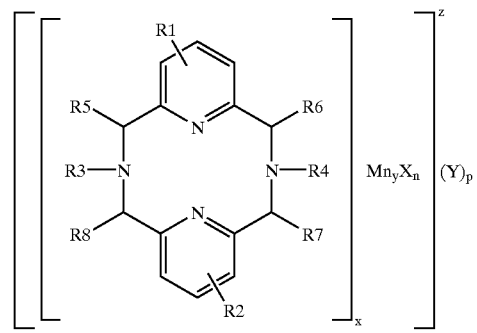

wherein Mn represents a manganese atom in oxidation state II, III, IV, or V, X is a group which is either a bridge or is not a bridge between manganese atoms, Y is a counter-ion, x and y being >=1, 0=<n=<3, and z being the charge of the metal complex, and p=z/ charge of Y; $R^1$ and $R_2$ being independently one or more ring substituents selected from hydrogen and electron donating and withdrawing groups, $R_3$, $R_4$, $R_5$, R6, $R_7$ and $R_8$ being independently hydrogen, alkyl, hydroxyalkyl, alkenyl or variants of any of these when substituted by one or more electron donating or withdrawing groups.

Throughout this specification. unless specifically stated to the contrary, all alkyl, hydroxyalkyl alkoxy, and alkenyl groups preferably have from 1 to 6, more preferably from 1 to 4 carbon atoms.

Moreover, throughout this specification, preferred electron donating groups include alkyl (e.g. methyl), alkoxy (e.g. methoxy) and unsubstituted-, monosubstituted and disubstituted amine groups. Preferred electron withdrawing groups include nitro, carboxy, sulphonyl and halo groups.

Thus, according to the values of x and y, the aforementioned preferred iron or manganese catalysts may be in the form of a monomer, dimer or oligomer. Without being bound by any theory, it has been conjectured that in the raw material or detergent composition state, the catalyst exists mainly or solely in monomer form but could be converted to dimer, or even oligomeric form, in the wash solution.

The catalysts of formula (I) have been found to be capable of a catalysing bleaching by both free oxygen and oxygen bleach compounds/systems Therefore, even without the presence of a chemical bleach/bleach system, catalysts according to the present invention can catalyse bleaching by atmospheric oxygen. Thus, compositions according to the present invention do not have to contain a bleach per se. However, they may also contain an oxygen bleach.

A fifth aspect of the present invention provides a bleaching process which comprises the step of treating a substrate with a source of free oxygen and/or an oxygen bleach, and a bleach catalyst of any of formulae (I), (II), (III), (IV) or (V).

Certain complexes of formula (IV) are described in the First and Second Koch References mentioned hereinbefore. Although not novel per se, their use as bleach catalysts is by no means obvious. However, all of the remaining complexes of formula (I) are believed to be novel and so in themselves constitute a third aspect of the present invention.

Thus, a fourth aspect of the present invention provides a bleach catalyst of formula (IV) as hereinbefore described, with the provisos that:

(i) if $R_1$, $R_2$ and $R_5$—$R_8$ are all hydrogen, $R_3$ and $R_4$ are both methyl; x=1, y=1, z=+1, n=1 and p=1; and Y is —$BPh_4$; then X is not Cl, catecholate or 3,5-di-tertbutyl-1,2-catecholate; and (ii) if $R_1$–$R_8$ are all hydrogen, and x=2, y=1, and n=0; then when z=+3 and p=3, Y is not $ClO_4^-$ and when z=+2 and p=2, Y is not —$BPh_4^-$.

Proviso (i) disclaims materials described as isolated, or formed in situ in the First Koch Reference. Proviso (ii) disclaims materials disclosed in the Second Koch Reference.

DETAILED DESCRIPTION OF THE INVENTION

Bleach Catalyst

In formula (IV) or formula (V) preferably, $R_1$ and $R_2$ are both hydrogen. $R_3$ and R4 are preferably $C_{1-4}$ alkyl, especially methyl. $R_5$–$R_8$ are each preferably hydrogen.

Preferably the oxidation state n is III.

X is preferably independently selected from $H_2O$, $OH^-$, $O_2^{2-}$, $O^{2-}HO_2^-$, $S^{2-}$, —SO—, $NR_9R_{10}^-$, $RCOO^-$, $NR_9R_{10}R_{11}$, $Cl^-$, $Br^-$, $F^-$, $N_3^-$, $SCN^-$, $N^{3-}$, or combinations thereof, wherein $R_9$, $R_{10}$ and $R_{11}$ are independently selected from H, $C_{1-4}$ alkyl and or aryl optionally substituted by one or more electron donating or withdrawing groups, X is preferably a halogen, especially a fluoride ion.

The cationic counter-ion equivalent Z is preferably absent.

The anionic counter-ion equivalent Y is preferably selected from $Cl^-$, $Br^-$, $I^-$, $NO_3^-$, $ClO_4^-$, $SCN^-$, $PF_6$—, $RSO_3^-$, $RSO_4^-$, $CF_3SO_3^-$, $BF_4^-$, $BPh_4^-$, and $OAc^-$.

Especially preferred examples of the catalyst of formula (IV) comprise salts of an iron dihalo-2,11 -diazo[3.3](2,6) pyridinophane and dihalo-4-methoxy-2,11-diazo[3.3](2,6) pyridinophane and mixtures thereof, especially in the form of their chloride salts.

An especially preferred example of the catalyst of formula (V) comprises a salt of a manganese dihalo, N,N'-dimethyl-2,11 -diazo[3.3](2,6)pyridinophane, especially in the form of its monohexafluorophosphate salt.

In typical washing compositions the level of [1] is such that the in-use level is from 1 μM to 50 mM, with preferred in-use levels falling in the range 10–100 μM.

Preparation

The bleach catalysts of formula (IV) wherein may for example be prepared by the following generalised reaction:

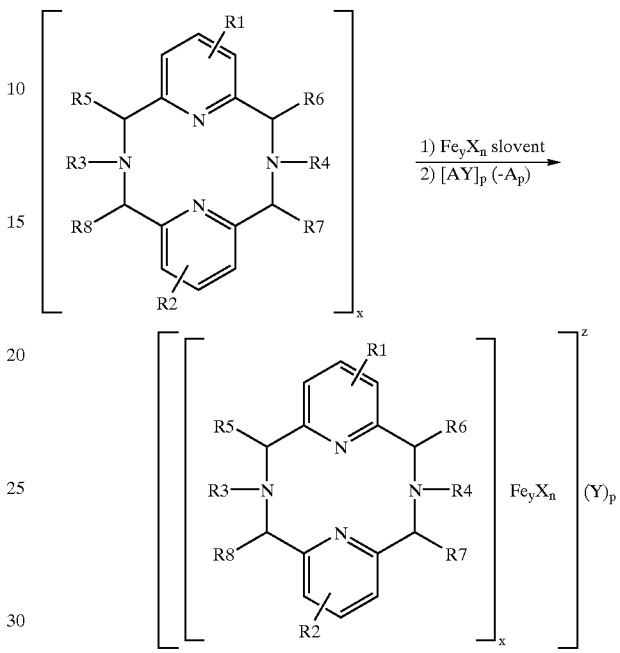

The bleach catalysts of formula (V) wherein may for example be prepared by the following generalised reaction:

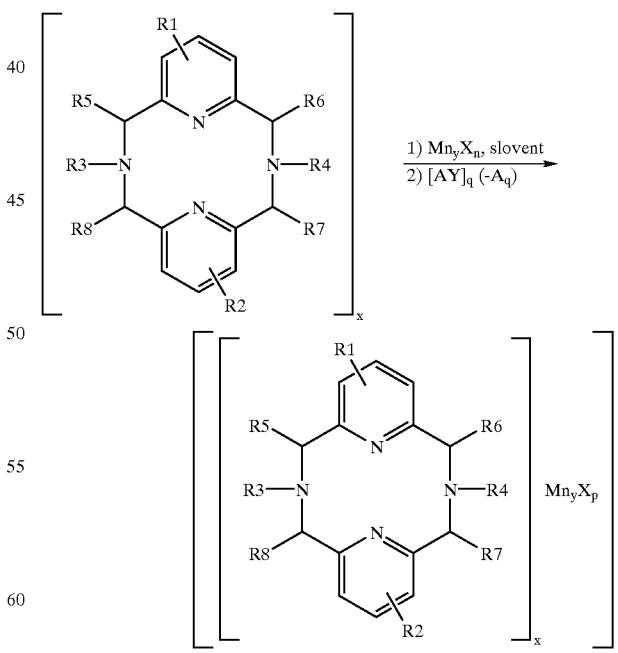

The ligands in the aforementioned generalised reaction schemes may for example be prepared by:

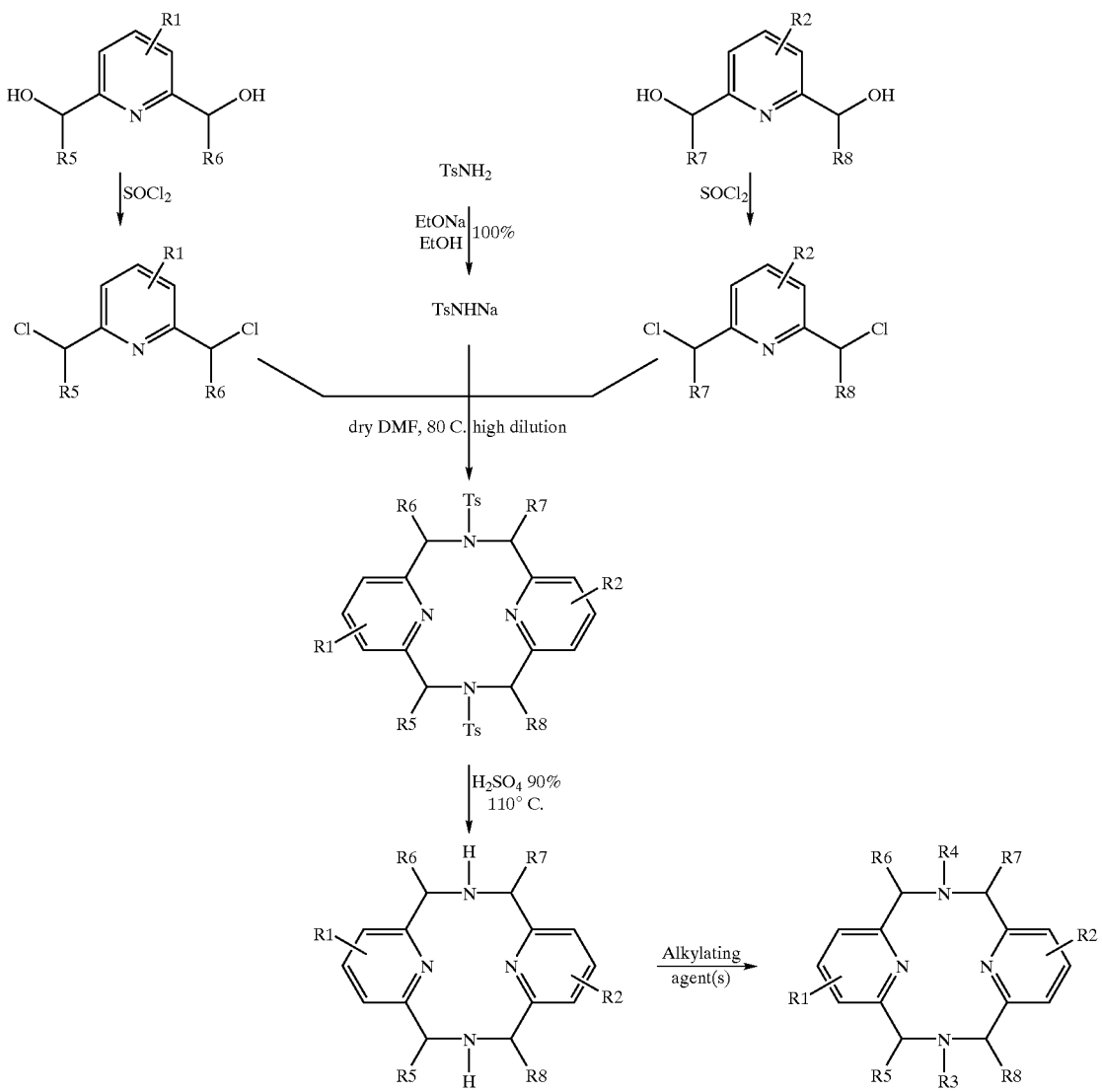

Persons skilled in the art will readily be capable of extrapolating these synthetic routes to all ligands of formula (I) ion pairs of formula (II) and complexes of formula (III)

Detergent and/or Bleach Compositions

The present invention has particular application in formulations to form a new and improved detergent and/or bleach compositions, comprising an oxygen bleach and/or surfactant. In the absence of a separate bleach, many materials within the scope of the invention are capable of catalysing bleaching by atmospeheric oxygen.

Oxygen Bleach

Preferably the oxygen bleach comprises a peroxygen compound. Generally speaking the peroxygen compound is selected from compounds of the general formula $R_{11}OOH$ wherein $R_{11}$, representing H or optionally substituted alkyl, the source of peroxygen is another inorganic or organic peroxysalt. Most preferably the R is H and the source of peroxygen is hydrogen peroxide.

More specifically, the peroxy bleaching compound may be a compound which is capable of yielding hydrogen peroxide in aqueous solution. Hydrogen peroxide sources are well known in the art. They include the alkali metal peroxides, organic peroxides such as urea peroxide, and inorganic persalts, such as the alkali metal perborates, percarbonates, perphosphates persilicates and persulphates. Mixtures of two or more such compounds may also be suitable.

Particularly preferred are sodium perborate tertrahydrate and, especially, sodium perborate monohydrate. Sodium perborate monohydrate is preferred because of its high active oxygen content. Sodium percarbonate may also be preferred for environmental reasons. The amount thereof in the composition of the invention usually will be within the range of about 5–35% by weight, preferably from 10–25% by weight.

Another suitable hydrogen peroxide generating system is a combination of a $C_1$–$C_4$ alkanol oxidase and a $C_1$–$C_4$ alkanol, especially a combination of methanol oxidase (MOX) and ethanol. Such combinations are disclosed in International Application PCT/EP 94/03003 (Unilever), which is incorporated herein by reference. Alkylhydroxy peroxides are another class of peroxy bleaching compounds.

Examples of these materials include cumene hydroperoxide and t-butyl hydroperoxide.

Organic peroxyacids may also be suitable as the peroxy bleaching compound. Such materials normally have the general formula:

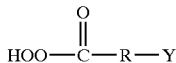

wherein R is an alkylene or substituted alkylene group containing from 1 to about 20 carbon atoms, optionally having an internal amide linkage; or a pheylene or substituted phenylene group; and Y is hydrogen, halogen, alkyl, aryl, an imido-aromatic or non-aromatic group, a COOH or

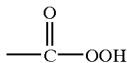

group or a quaternary ammonium group.

Typical monoperoxy acids useful herein include, for example:
(i) peroxybenzoic acid and ring-substituted peroxybenzoic acids, e.g. peroxy-a-naphthoic acid;
(ii) aliphatic, substituted aliphatic and arylalkyl monperoxyacids, e.g. peroxylauric acid, peroxystearic acid and N,N-phthaloylaminoperoxy caproic acid (PAP); and
(iii) 6-octylamino-6-oxo-peroxyhexanoic acid.

Typical diperoxyacids useful herein include, for example:
(iv) 1,12-diperoxydodecanedioic acid (DPDA);
(v) 1,9-diperoxyazelaic acid;
(vi) diperoxybrassilic acid; diperoxysebasic acid and diperoxyisophthalic acid;
(vii) 2-decyldiperoxybutane-1,4-diotic acid; and
(viii) 4,4'-sulphonylbisperoxybenzoic acid.

Also inorganic peroxyacid compounds are suitable, such as for example potassium monopersulphate (MNS). If organic or inorganic peroxyacids are used as the peroxygen compound, the amount thereof will normally be within the range of about 2–10% by weight, preferably from 4–8% by weight.

All these peroxy compounds may be utilised alone or in conjunction with a peroxyacid bleach precursor and/or an organic bleach catalyst not containing a transition metal. Generally, the bleaching composition of the invention can be suitably formulated to contain from 2 to 35%, preferably from 5 to 25% by weight, of the peroxy bleaching agent.

Peroxyacid bleach precursors are known and amply described in literature, such as in the British Patents 836988, 864,798; 907,356; 1,003,310 and 1,519,351; German Patent 3,337,921; EP-A-0185522; EP-A-0174132; EP-A-0120591; and U.S. Pat. No. 1,246,339; 3,332,882; 4,128,494; 4,412, 934 and 4,675,393.

Another useful class of peroxyacid bleach precursors is that of the cationic i.e. quaternary ammonium substituted peroxyacid precursors as disclosed in U.S. Pat. No. 4,751, 015 and 4,397,757, in EP-A-0284292 and EP-A-331,229. Examples of peroxyacid bleach precursors of this class are:
2-(N,N,N-trimethyl ammonium)ethyl sodium-4-sulphonphenyl carbonate chloride—(SPCC);
N-octyl,N,N-dimehyl-N10-carbophenoxy decyl ammonium chloride —(ODC);
3-(N,N,N-trimethyl ammonium)propyl sodium-4-sulphophenyl carboxylate; and
N,N,N-trimethyl ammonium toluyloxy benzene sulphonate.

A further special class of bleach precursors is formed by the cationic nitriles as disclosed in EP-A-303,520 and in European Patent Specification No.s 458,396 and 464,880.

Any one of these peroxyacid bleach precursors can be used in the present invention, though some may be more preferred than others.

Of the above classes of bleach precursors, the preferred classes are the esters, including acyl phenol suphonates and acyl alkyl phenol sulphonates; the acyl-amides; and the quaternary ammonium substituted peroxyacid precursors including the cationic nitriles.

Examples of said preferred peroxyacid bleach precursors or activators are sodium4-benzoyloxy benzene sulphonate (SBOBS); N,N,N'N'-tetraacetyl ethylene diamine (TAED); sodium-1-methyl-2-benzoyloxy benzene-4-sulphonate; sodium-4-methyl-3-benzoyloxy benzoate; SPCC; trimethyl ammonium toluyloxy-benzene sulphonate; sodium nonanoyloxybenzene sulphonate (SNOBS); sodium 3,5,5-trimethyl hexanoyl-oxybenzene sulphonate (STHOBS); and the substituted cationic nitriles.

The precursors may be used in an amount of up to 12%, preferably from 2–10% by weight, of the composition.

As an alternative to the above described peroxide generating systems, molecular oxygen may be used as the oxidant.

Normally, the amount of peroxygen compound will be in an amount relative to the catalyst of formula (I) such that the catalyst represent from 0.1% to 10% by weight of the peroxygen compound. Preferred molar ratios of peroxygen compound to catalyst are 10000:1 to 1000:1.

Surface-active Material

Detergent compositions according to the present invention generally contain surface-active material in an amount of from 10 to 50% by weight. Said surface-active material may be naturally derived, such as soap, or a synthetic material selected from anionic, nonionic, amphoteric, zwitterionic, cationic actives and mixtures thereof. Many suitable actives are commercially available and are fully described in the literature, for example in "Surface Active Agents and Detergents", Volumes I and II, by Schwartz, Perry and Berch.

Typical synthetic anionic surface-actives are usually water-soluble alkali metal salts of organic sulphates and sulphonates having alkyl radicals containing from about 8 to about 22 carbon atoms, the term alkyl being used to include the alkyl portion of higher aryl radicals. Examples of suitable synthetic anionic detergent compounds are sodium and ammonium alkyl sulphates, especially those obtained by sulphating higher ($C_8$–$C_{18}$) alcohols produced, for example, from tallow or coconut oil; sodium and ammonium alkyl ($C_9$–$C_{10}$) benzene sulphonates, particularly sodium linear secondary alkyl ($C_{10}$–$C_{15}$) benzene sulphonates; sodium alkyl glyceryl ether sulphates, especially those ester of the higher alcohols derived from tallow or coconut oil fatty acid monoglyceride sulphates and sulphonates; sodium and ammonium salts of sulphuric acid esters of higher ($C_9$–$C_{10}$) fatty alcohol alkylene oxide, particularly ethylene oxide, reaction products; the reaction products of fatty acids such as coconut fatty acids esterified with isethionic acid and neutralised with sodium hydroxide; sodium and ammonium salts of fatty acid amides of methyl taurine; alkane monosulphonates such as those derived by reacting alpha-olefins ($C_8$–$C_{20}$) with sodium bisulphite and those derived by reaction paraffins with $SO_2$ and $C_{12}$ and then hydrolysing with a base to produce a random sulphonate; sodium and ammonium $C_7$–$C_{12}$ dialkyl sulphoscinates; and olefin sulphonates which term is used to describe material made by reacting olefins, particularly $C_{10}$–$C_{20}$ alpha-olefins, with $SO_3$ and then neutralising and hydroysing the reaction product. The preferred anionic detergent compounds are sodium ($C_{10}$–$C_{15}$) alkylbenzene sulphonates, sodium ($C_{16}$–C18) alkyl ether sulphates.

Examples of suitable nonionic surface-active compounds which may be used, preferably together with the anionic surface-active compounds, include, in particular, the reaction products of alkylene oxides, usually ethylene oxide, with alkyl ($C_6$–$C_{22}$) phenols, generally 5–25 EO, i.e. 5–25 units of ethylene oxides per molecule; and the condensation products of aliphatic ($C_8$–$C_{18}$) primary or secondary linear or branched alcohols with ethylene oxide, generally 2–30 EO. Other so-called nonionic surface-actives include alkyl polyglycosides, sugar esters, long-chain tertiary amine oxides, long-chain tertiary phosphine oxides and dialkyl sulphoxides.

Amphoteric or zwitterionic surface-active compounds can also be used in the compositions of the invention but this is not normally desired owing to their relatively high cost. If any amphoteric or zwitterionic detergent compounds are used, it is generally in small amounts in compositions based on the much more commonly used synthetic anionic and nonionic actives.

As disclosed by EP-A-544,490, the performance of the hereinbefore described bleach catalyst, may be dependent upon the active detergent system and the builder system present in the detergent bleach composition of the invention.

The detergent bleach composition of the invention will preferably comprise from 1–15% wt of anionic surfactant and from 10–40% by weight of nonionic surfactant. In a further preferred embodiment the detergent active system is free from $C_{16}$–$C_{12}$ fatty acids soaps.

Detergency Builder

The composition of the invention may also contain a detergency builder in an amount of from about 5–80% by weight, preferably from about 10–60% by weight.

Builder materials may be selected from 1) calcium sequestrant materials, 2) precipitating materials, 3) calcium ion-exchange materials and 4) mixtures thereof.

Examples of calcium sequestrate builder materials include alkali metal polyphosphates, such as sodium tripolyphosphate; nitrilotriacetic acid and its water-soluble salts; the alkali metal salts of carboxymethyloxy succinic acid, ethylene diamine tetraacetic acid, oxydisuccinic acid, mellitic acid, benzene polycarboxylic acids, citric acid; and polyacetal carboxylates as disclosed in U.S. Pat. Nos. 4,144,226 and 4,146,495.

Examples of precipitating builder materials include sodium orthophosphate and sodium carbonate.

Examples of calcium ion-exchange builder materials include the various types of water-insoluble crystalline or amorphous aluminosilicates, of which zeolites are the best known representatives, e.g. zeolite A, zeolite B (also known as zeolite P), zeolite C, zeolite X, zeolite Y and also the zeolite P type as described in EP-A-0384070.

In particular, the compositions of the invention may contain any one of the organic and inorganic builder materials, though, for environmental reasons, phosphate builders are preferably omitted or only used in very small amounts.

Typical builders usable in the present invention are, of example, sodium carbonate, calcite/carbonate, the sodium salt of nitrilotriacetic acid, sodium citrate, carboxymethyloxy malonate, carboxymethyloxy succinate and the water-insoluble crystalline or amorphous aluminosilicate builder material, each of which can be sued as the main builder, either alone or in admixture with minor amounts of other builders or polymers as co-builder.

It is preferred that the composition contains not more than 5% by weight of a carbonate builder, expressed as sodium carbonate, more preferable not more than 2.5% by weight to substantially nil, if the composition pH lies in the lower alkaline region of up to 10.

Other Ingredients

Apart from the components already mentioned, the detergent bleach composition of the invention can contain any of the conventional additives in amounts of which such materials are normally employed in fabric washing detergent compositions. Examples of these additives include buffers such as carbonates, lather boosters, such as alkanolamides, particularly the monoethanol amides derived from palmkernel fatty acids and coconut fatty acids; lather depressants, such as alkyl phosphates and silicones; anti-redeposition agents, such as sodium carboxymethyl cellulose and alkyl or substituted alkyl cellulose ethers; stabilisers, such as phosphonic acid derivatives (i.e. Dequest® types); fabric softening agents; inorganic salts and alkaline buffering agents, such as sodium sulphate, sodium silicate etc.; and usually in very small amounts, fluorescent agents; perfumes; enzymes, such as proteases, cellulases, lipases, amylases and oxidases; germicides and colorants.

When using a hydrogenperoxide source, such as sodium perborate or sodium percarbonate, as the bleaching compound, it is preferred that the composition contains not more than 5% by weight of a carbonate buffer, expressed as sodium carbonate, more preferable not more than 2.5% by weight to substantially nil, if the composition pH lies in the lower alkaline region of up to 10.

Of the additives, transition metal sequestrants, such as EDTA and the phosphonic acid derivatives, e.g. ethylene diamine tetra-(methylene phosphonate) —EDTMP—are of special importance, as not only do they improve the stability of the catalyst/$H_2O_2$ system and sensitive ingredients, such as enzymes, fluorescent agents, perfumes and the like, but also improve the bleach performance, especially at the higher pH region of above 10, particularly at pH 10.5 and above.

Product Form

Compositions according to the present invention (whether or not detergent bleach compositions) may be formulated in any form, e.g. as granulates (which may be prepared by spray drying or non-spray drying granulation), as powder additives for dosing into a granulation process or post-dosing to a granulated product, as pills or tablets or as aqueous or non-aqueous liquids.

The invention will now be further illustrated by way of the following non-limiting Examples.

EXAMPLE 1

[Fe((4OMe)LN$_4$H$_2$)Cl$_2$]Cl

The Example is a catalyst of formula (I) wherein:

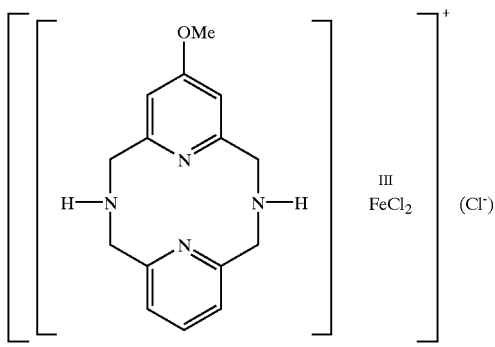

R$_2$–R=H; R$_1$=4-MeO; x=1; y=1; z=1; X=Cl, n=2; Y=Cl$^-$, p=1.

The (unmethoxylated) basic ligand will be referred to by the abbreviation LN$_4$.

(i) Syntheses of the Ligand: ((4OMe)LN$_4$H$_2$)2,11-diaza[3.3]-(4-methoxy)(2,6)pyridinophane:

4-chloro-2.6-pyridyl dimethyl ester (2). A mixture of 4-hydroxy-2,6-pyridine dicarboxylic acid (12.2 g, 60 mmoles) and PCl$_5$ (41.8 g, 200 mmoles) in 100 ml of CCl$_4$ was refluxed until the evolution of HCl ceased. Absolute methanol (50 ml) was slowly added. After cooling, all the volatile material was removed. The mixture was then poured into 200 ml of water and ice. The diester crystallised immediately and was collected by filtration (70%). $^1$H NMR (200 MHz, H$_2$O)δ 7.60 (2H, s), 4.05(6H, s).

4-methoxy-2.6-pyridine dimethanol (4). Metallic sodium (1 g, 44 mmoles) was dissolved into 200 ml of dry methanol. 4-chloro-2,6-pyridyl dimethyl ester (9.2 g, 40 mmoles) was then added and the mixture was refluxed for 3 hours to obtain pure 4-methoxy-2,6-pyridyl dimethyl ester. To this solution, at RT, NaBH$_4$ (9.1 g, 240 mmoles) was added in small portions and the mixture was refluxed for 16 hours. Acetone (30 ml) was then added and the solution refluxed for an additional 1 hour. After all the volatile material was removed, the residue was heated with 60 ml of a saturated NaHCO$_3$/Na$_2$CO$_3$ solution. After dilution with 80 ml of water, the product was continuously extracted with CHCl$_3$ for 2–3 days. Evaporation of the CHCl$_3$ yielded 83% of 4-methoxy-2,6-pyridine dimethanol. $^1$H NMR (200 MHz, H$_2$O)δ 6.83(2H,s), 5.30(2H,s), 4.43(4H,s), 3.82(3H, s).

4-methoxy-2.6dichloromethylpyridine (5). This synthesis is carried out according to the methods of Baker W. et al, J. Chem. Soc. (1958) 3594 and Lee G., J. Org. Chem., (1996), 61, 8304.

N,N'-ditosyl-2,11-diaza[3.3]-(4-methoxy)(2,6)pyridinophane. the procedure is similar to that described in the literature. The crude product obtained is practically pure (yield=95%.)

$^1$H-NMR (CDCl$_3$, 250 MHz): 7.72(4H, d, J=7Hz), 7.4 (1H, t, J=6Hz), 7,35(4H, d, J=7Hz), 7.1(1H, d, J=6Hz), 6.57(2H, s), 4.45(4H, s), 4.35(4H, s) 3.65(3H, s), 2.4(6H, s).

2.11-diaza[3.3]-(4-methoxy)(2,6)pyridinophane. The procedure is similar to the one described previously. The crude product obtained is purified by chromatography (alumina, CH$_2$Cl$_2$/MeOH 95:5), yield=65%.

$^1$H-NMR (CDCl$_3$, 250 MHz): 7.15($^1$H, t, J=6Hz), 6.55 (1H, d, J=6Hz), 6.05(2H, s), 3.95(4H, s), 3.87(4H, s), 3.65(3H. s).

Mass spectrum (EI): M$^+$=270(100%).

(ii) Syntheses of the Complex: [Fe(40MeLN$_4$H$_2$)Cl$_2$]Cl 270 mg of 2,11-diaza[3.3]-(4-methoxy)(2,6)pyridinophane (1 mmole) were dissolved in 15 ml of dry THF. To this solution was added a solution of 270 mg of FeCl$_3$.6H$_2$O (1 mmoles) in 5 ml of MeOH. The resulting mixture is evaporated to dryness and the solid product is dissolved in 10 ml of AcN with a minimum of MeOH. Slow diffusion of THF give 300 mg of brown crystals, yield=70%. Elemental analysis for C$_{15}$H$_{18}$N$_4$Cl$_3$OFe0,5MeOH (found/theoretical): C=41.5/41.61 H=4.46/4.52 N=12.5/12.08 IR (KBr pellets, cm$^{-1}$): 3545, 3414, 3235, 3075, 2883, 1615, 1477, 1437, 1340, 1157, 1049, 883, 628, 338.

EXAMPLE 2

Synthesis of the Complex [Fe(LN$_4$H$_2$)Cl$_2$]Cl

This Example is a catalyst of formula (I) wherein:

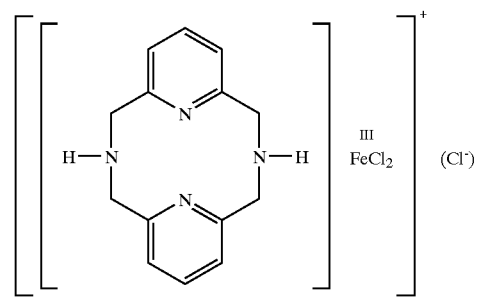

R$_1$–R$_8$=H; x=1; y=1; z=1; X=Cl, n=2; Y=Cl$^-$, p=1

240 mg of LN$_4$H$_2$ (1 mmoles) were dissolved in 15 ml of dry THF. To this solution was added a solution of 270 mg of FeCl$_3$.6H$_2$O (1 mmole) in 5 ml of MeOH. The resulting mixture is stirred and gives spontaneously 340 mg of yellow powder, yield=85%. IR (KBr pellets, cm$^{-1}$): 3445, 3031, 2851, 1629, 1062, 1473, 1427, 1335, 1157, 1118, 1045, 936, 796, 340, 318.

EXAMPLE 3

Difluoro[N,N'dimethyl-2,11-diaza[3.3](2,6)pyridinophane]manganese(III) hexafluorophosphate The Example is a catalyst of formula (I) wherein:

R$_1$ = R$_2$ = R$_{5-8}$ = H
R$_3$ = R$_4$ = Me
x = 1
y = 1
n = 2
z = 1
X = F$^-$, m = 2
Y = PF$^-_6$, p = 1

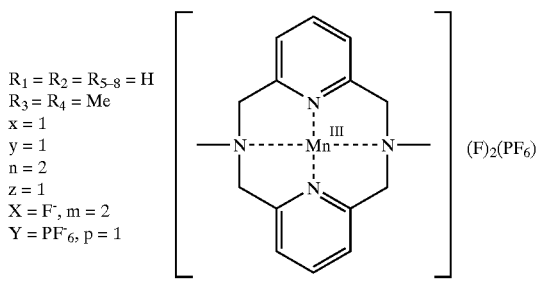

(i) Synthesis of the Ligand: N,N'dimethyl-2,11-diaza[3.3](2,6)pyridinophane 2.6-dichloromethylpyridine. A mixture of 2,6-dimethanolpyridine (5 g, 36 mmoles) and 75 ml of SOCl$_2$ was refluxed for 4 hours. The mixture was concentrated (half volume). Toluene was added (50 ml). The solid formed after cooling was then filtered and dissolved in water and the solution neutralised with NaHCO$_3$. The solid obtained is filtered and dried (65%). $^1$H NMR (200 MHz CDCl$_3$)δ 6 7.8(1H,t, J=7Hz), 7.45(2H,d, J=7 Hz), 4.7(4H, s).

Sodium p-toluenesulfonamidure. To a mixture of Na° in dry EtOH (0.7 g, 29 mmoles) was added p-toluenesulfonamide (5 g, 29 mmoles) and the solution was refluxed for 2 hours. After cooling, the solid obtained was filtered, washed with EtOH and dried (quantitative yield).

N,N'-ditosyl-2,11-diaza[3.3](2.6)pyridinophane. To a solution of sodium p-toluenesulfonamidure (1.93 g, 10 mmoles) in 200 ml of dry DMF at 80° C. was slowly added 2,6-dichloromethylpyridine (1.76 g, 10 mmoles). After 1 hour a new portion of sodium p-toluenesulfonamidure was added (1.93 g) and the final mixture stirred at 80° C. for an addition 4 hours. The solution was then evaporated to dryness. The solid obtained was washed with water and then with EtOH and finally crystallised in an CHCl3/MeOH mixture. The solid obtained is filtered and dried. The yield of (15) was 55%. $^1$H NMR (200 MHz, CDCl$_3$)δ 7.78(4H, d, J=6Hz), 7.45(6H,m), 7.15(4,d, J=6Hz), 4.4(8H, s), 2.4(6H, s)

2.11-diaza[3.3](2,6)pyridinophane. A mixture of N,N'-ditosyl-2,11-diaza[3.3](2,6)pyridinophane (1.53 g, 2.8 mmoles) and 14 ml of H$_2$SO$_4$90% was heated at 110° C. for 2 hours. The solution, cooled and diluted with 14 ml of water, was then carefully poured into a saturated NaOH solution. The solid formed is extracted with chloroform. The organic layer is evaporated to dryness to yield 85% of 2,11-diaza[3.3](2,6)pyridinophane. $^1$H NMR (200 MHz, CDCl$_3$)δ 7.1(2H,t, J=7Hz), 6.5(4H,d, J=7 Hz), 3.9(8H, s).

N,N'-dimethyl-2,11diaza[3.3](2.6)pyridinophane. A mixture of 2,11-diaza[3.3](2,6)pyridinophane (0.57 g, 2.4 mmoles), 120 ml of formic acid and 32 ml of formaldehyde (32% in water) was refluxed for 24 hours. Concentrated HCl (10 ml) were added and the solution evaporated to dryness. The solid was dissolved in water and basified with NaOH 5M, and the resulting solution was extracted with CHCl$_3$. The solid obtained was purified by chromatography on alox (CH$_2$Cl$_2$+1% MeOH) to yield 51% of N,N'-dimethyl-2,11-diaza[3.3](2,6)pyridinophane. $^1$H NMR (200 MHz, CDCl$_3$)δ 7.15(2H,t, J=7Hz), 6.8(4H,d, J=7 Hz), 3.9(8H, s), 2.73 (6H,s).

(ii) Synthesis of the Complex:

MnF$_3$(41.8 mg, 373 mmoles) was dissolved in 5 ml of MeOH, and N,N'-dimethyl-2,11diazhexa[3.3](2,6) pyridinophane (0.1 g, 373 mmoles) was added with 5 ml of THF. After 30 minutes of stirring at RT, 4 ml of THF saturated in NBu$_4$PF$_6$ were added, and the solution left without stirring until the crystallisation was finished. The product was collected by filtration to yield 80% of complex. Elemental analysis (found, theoretical): %C (38.35, 37.94), %N (11.32, 11.1), %H (3.75, 3.95). IR (KBr pellet, cm$^{-1}$): 3086, 2965, 2930, 2821, 1607, 1478, 1444, 1425, 1174, 1034, 1019, 844, 796, 603, 574, 555. UV-Vis (CH$_3$CN, λin nm, ε): 500, 110; 850, 30; (CH$_3$CN/H$_2$O:1/1, λin nm, ε): 465, 168; 850, 30.

EXAMPLE 4

(i) Synthesis of bis(4OMe)LN$_4$Ts$_2$:

The procedure is similar to that described in the literature. (B. Alfa, E. Anklam, R. Deschenaux, J. M. Lehn, M. Pitraskiwicz; *Helv. Chim. Acta*, 1988, 71, 1042.)

The starting pyridine ring is the 2,6-dichloromethyl4-OMe-pyridine. (D. J. Markees, G. W. Kidder; *J. Am. Chem. Soc.*, 1956, 78,4130, Lee G., J. Org. Chem., (1996), 61, 8304 and W. Baker, K. M. Buggle, B. A. M. Watkins; *J Chem. Soc.*, 1958, 3594.)

The crude product obtained is purified by a column chromatography (silica, Ethyl Acetate+5% NEt$_3$), yield=85%.

$^1$H-NMR (CDCl$_3$, 250 MHz): 7.75(4H,d,J$^3$=7Hz), 7.4 (4H,d,J$^3$=7Hz), 6.75(4H,s), 4.45(8H,s), 3.75(6H,s), 2.5(6H, s).

(ii) Synthesis of bis(4OMe)LN$_4$H$_2$:

The product is deprotected as described in the literature. (B. Alfa, E. Anklam, R. Deschenaux, J. M. Lehn, M. Pitraskiwicz; *Helv. Chim. Acta*, 1988, 71 1042.)

The starting material is the bis(4OMe)LN$_4$Ts$_2$; yield= 90%.

$^1$H-NMR (CDCl$_3$, 250 MHz) 5.95(4H, s), 3.8(2H, s), 3.75(8H, s), 3.65(6H,s).

(iii) Synthesis of [Fe(bis(4OMe)LN$_4$H$_2$)Cl$_2$]Cl:

150 mg of ligand (0.5 mmole) were dissolved in 15 ml of dry CH$_3$CN and 3 ml of CH$_2$Cl$_2$. To this solution is added a solution of 1355 mg of FeCl$_3$.6H$_2$O (0.5 mmoles) in 5 ml of CH$_3$CN. The resulting mixture filtered an devaporated to dryness. The crude product is dissolved in a minimum of CH$_3$CN and slow diffusion of THF give 300 mg of brown crystals, yield=70%. Elemental analysis for C$_{16}$H$_{20}$N$_4$Cl$_3$O$_2$Fe.1 MeOH (found/theoretical): C=41.4/41.3 H=4.7/4.86 N=11.4/11.33 IR (KBr pellets, cm$^{-1}$): 3425, 3072, 2880, 1614, 1477, 1437, 1339, 1043, 880, 335.

(iv) Synthesis of [LN$_4$H$_2$Fecat](BPh$_4$)CH$_3$OH:

38 mg (0.23 mmol) of FeCl$_3$ in 10 ml of methanol are added on a solution of 60.5 mg (0.25 mmol) of LN$_4$H$_2$ in 10 ml of methanol. The resulting solution is put under argon in a schlenck. A solution of 26 mg of catechol (0.23 mmol) is degazed. MeOH is deprotonated under argon by 70 μl of Et$_3$N and added under Ar on the LN$_4$H$_2$FeCl$_3$ solution. A deep blue coloration appears. 85 mg (0.25 mmol) of NaBPh$_4$ in methanol and under Ar are added and the blue powder obtained is collected by filtration under Ar. UV:

Elementary analysis: C: 72.8, H: 5.7, N: 7.4, Fe: 6.95.

Expected for [LN$_4$H$_2$Fecat](BPh$_4$)CH$_3$OH, C: 71.4, H: 5.9, N: 7.4, Fe: 7.3.

Expected for [LN$_4$H$_2$Fecat](BPh$_4$), C: 73.05, H: 5.57, N: 7.74, Fe: 7.72.

(v) Synthesis of [LN$_4$H$_2$Fe(DTBcat)](BPh$_4$):

The same experimental procedure as (iv) allowed [LN$_4$H$_2$Fe(DTBcat)](BPh$_4$) to be obtained.

Abbreviations cat=catechol(ate)
DTBcat=diterbutylcatechol(ate)
Ts=tosyl

What is claimed is:

1. A bleach catalyst of formula (IV):

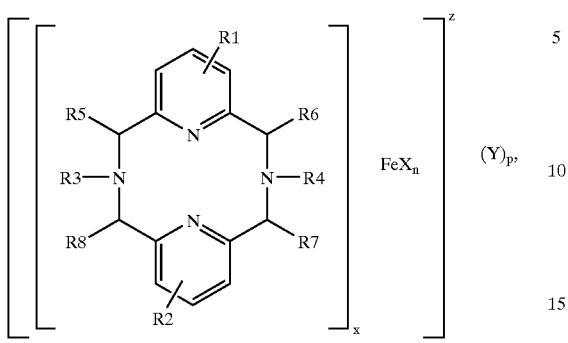

wherein Fe represents an iron atom in oxidation state II or III, X is a group which is either a bridge or is not a bridge between iron atoms, Y is a counter-ion, x and y being >=1, 0=<n=<3, and z being the charge of the metal complex, and p=z/ charge of Y; $R_1$ and $R_2$ being independently one or more ring substituents selected from hydrogen and electron donating and withdrawing groups selected from: halo, $C_{1-6}$alkoxy, hydroxy, hydroxyalkyl, (optionally mono-or di-substituted) amine groups, (optionally mono- or di-substituted) thiol groups, carboxyl, ester, amide, substituted carbonyl groups in general, nitrile, nitro, (optionally substituted) sulphonyl, alkenyl, aryl, quarternary ammonium (+) and sulphonium (+);

$R_3$–$R_8$ being independently hydrogen, alkyl, hydroxyalkyl, alkenyl or variants of any of these when substituted by one or more electron donating or withdrawing groups selected from: halo, $C_{1-6}$alkoxy, hydroxy, hydroxyalkyl, (optionally mono-or di-substituted) amine groups, (optionally mono- or di-substitued) thiol groups, carboxyl, ester, amide, substituted carbonyl groups in general, nitrile, nitro (optionally substituted) sulphonyl, alkenyl, aryl, quarternary ammonium (+) and sulphonium (+) with the proviso that in the bleach catalyst of formula (IV) the following ligand is excluded:

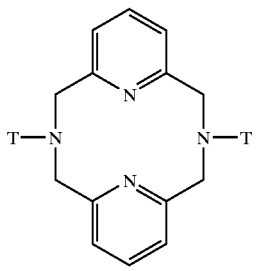

wherein in case 1, both T=$CH_3$,
wherein in case 2, T=H or

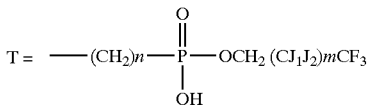

where m is 0 or an integer of 1, 2, 3 or 4;
n is an integer of 1, 2 or 3;
$J_1$ and $J_2$=H or F, wherein in case 3, T=—$CH_2$COOH, —$CH_2$P(O)OHW
where W is OH or, C1–C5-alkyl or —O—(C1–C5)-alkyl, or

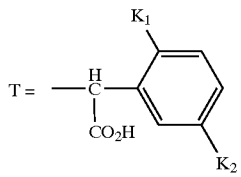

where $K_1$=—OH or —$OCH_3$ $K_2$ is —$NO_2$, —$NH_3$, isothiocyanato, semicarbazido, thiosemicarbazido, maleimido, bromoacetamido or carboxyl.

2. A bleach catalyst of formula (IV) as defined in claim 1, with the priviso that:
(i) if $R_1$, R2 and $R_5$–$R_8$ are all hydrogen, $R_3$ and $R_4$ are both methyl;
x=1, y=1, z=+1, n=1 and p1; and
Y is —$BPh_4^-$;
then X is not C1, catecholate or 3,5-di-tertbutyl-1,2-catecholate, and
(ii) if $R_1$–$R_8$ are all hydrogen; arid
x=2, y=1, and n=0;
then when z=+3 and p=3, Y is not $ClO_4^-$. and when z=+2 and p=2, Y is not —$BPh_4^-$.

3. A bleach catalyst according to claim 1, wherein $R_1$ and $R_2$ are both hydrogen, $R_3$ and $R_4$ are independently $C_{1-4}$ alkyl and $R_5$–$R_8$ are each hydrogen.

4. A bleach catalyst according to claim 1, wherein the metal is in the III oxidation state.

5. A bleach catalyst according to claim 1, wherein X is selected from $H_2O$, $OH^-$, $O_2^{2-}$, $O^{2-}$, $HO_2^-$, $SH^-$, $S^{2-}$, —SO—, $NR_9R_{10}^-$, carboxylate, $NR_9R_{10}R_{11}$, $Cl^-$, $Br^-$, $F^-$, $N_3^-$ and combinations thereof, wherein $R_9$, $R_{10}$ and $R_{11}$ are independently selected from H, $C_{1-6}$alkyl and aryl optionally substituted by one or more electron withdrawing and/or donating groups.

6. A bleach catalyst according to claim 1, wherein Z is absent.

7. A bleaching composition comprising a catalyst according to claim 1, wherein Y is selected from $ClO_4^-$, $SCN^-$, $PF_6$—, sulphonate, sulphate, $CF_3SO_3^-$, $BF_4^-$, $BPh_4^-$, and $OAc^-$.

8. A bleaching composition comprising a bleach catalyst according to claim 1 and comprising at least one other component selected from surfactants and oxygen bleaches.

9. A process of bleaching and/or cleaning a substrate, the process comprising treating the substrate with a bleach catalyst according to claim 1.

* * * * *